| United States Patent [19]
Lesher et al.

[11] 4,415,580
[45] Nov. 15, 1983

[54] CERTAIN 2-(1H)-PYRIDINONES CARDIOTONIC COMPOSITIONS CONTAINING SAME AND METHOD OF USING SAME

[75] Inventors: George Y. Lesher, Schodack; Baldev Singh, East Greenbush, both of N.Y.

[73] Assignee: Sterling Drug Inc., New York, N.Y.

[21] Appl. No.: 404,454

[22] Filed: Aug. 2, 1982

[51] Int. Cl.$^3$ .................... A61K 31/44; C07D 213/50
[52] U.S. Cl. .................................. 424/263; 546/288; 546/298; 546/123
[58] Field of Search ................. 546/288, 298; 424/263

[56] References Cited

PUBLICATIONS

Chemical Abstracts 72, 12,615d (1970).
Ogata et al. [Chem. Pharm. Bull. 20, 2264 (1972)].
Hawes et al. [J. Med. Chem. 16, 849 (1973)].
Hawes et al. [J. Heterocycl. Chem. 11, 151 (1974)].
Moller et al. [Ann. 612, 153 (1957)].

Primary Examiner—Alan L. Rotman
Attorney, Agent, or Firm—Robert K. Bair; B. Woodrow Wyatt; Paul E. Dupont

[57] ABSTRACT

1-R''-3-Q-4-R'-5-R-1,6-naphthyridin-2(1H)-ones (I) or salts thereof, where R is lower-alkyl, R' is hydrogen or methyl, R'' is hydrogen or lower-alkyl, and Q is hydrogen, hydroxy, amino, cyano, carbamyl, carboxy or aminocarbamyl, are useful as cardiotonic agents (I, Q is hydrogen, hydroxy, amino, cyano or carbamyl) and/or intermediates therefor (I, Q is carboxy, aminocarbamyl, hydrogen, amino, cyano or carbamyl). Also shown are 3-Q''-4-R'-5-(RCO)-6-[2-(di-lower-alkylamino)ethenyl]-2(1H)-pyridinones (II) or salts thereof, where R and R' are as above and Q' is hydrogen or cyano, which are useful as cardiotonics (II, Q' is hydrogen) and/or intermediates (II, Q' is cyano or hydrogen). Processes for preparing the compounds of formulas I and II are shown.

14 Claims, No Drawings

CERTAIN 2-(1H)-PYRIDINONES CARDIOTONIC COMPOSITIONS CONTAINING SAME AND METHOD OF USING SAME

CROSS-REFERENCE TO RELATED APPLICATION

Lesher and Singh copending U.S. Patent Application Ser. No. 357,872, filed Mar. 15, 1982, discloses and claims compounds used herein as intermediates, namely, 3-Q-4-$R_2$-5-(lower-alkanoyl)-6-methyl-2(1H)-pyridinones, cardiotonic agents, where Q is hydrogen or cyano and $R_2$ is hydrogen or methyl.

BACKGROUND OF THE INVENTION (a) Field of the Invention

This invention relates to 5-(lower-alkyl)-1,6-naphthyridin-2(1H)-ones, their cardiotonic use and their preparation.

(b) Description of the Prior Art

Chemical Abstracts 72, 12,615d (1970) is reproduced as follows: "Chemotherapeutics. IV. 1,6-Naphthyridine N-oxides. Takahashi Torizo; Hamada Yoshiki; Takeuchi Isao; Uchiyama Hideko (Fac. Pharm., Meijo Univ., Nagoya, Japan). Yakugaku Zasshi 1969, 89(9), 1260-5 (Japan). Various reaction conditions were examd. for the formulation of I, II, III, and IV by the application of hydrogen peroxide to 1,6-naphthyridine in HOAc soln.

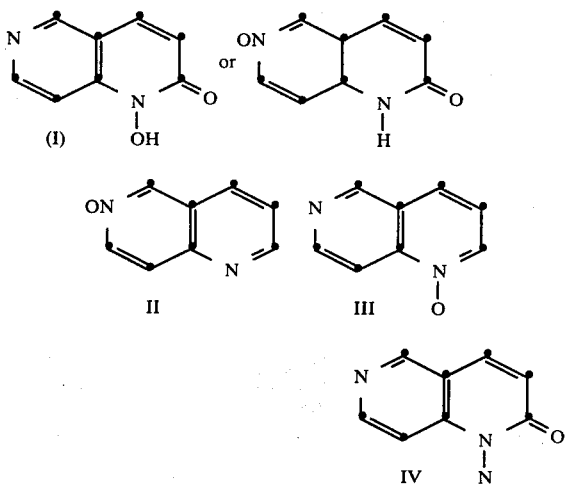

Ir, uv, NMR, and mass spectra of these four compds. were measured to detect their structure, which was detd. by chem. methods such as redn. with Raney Ni. Antibacterial action of I, II, and III was examd."

2-Hydroxy-3-methyl-1,6-naphthyridine, the tautomeric form of 3-methyl-1,6-naphthyridin-2(1H)-one, was reportedly prepared by Ogata et al. [Chem. Pharm. Bull. 20, 2264 (1972)] in two steps by first photocyclization of N-(4-pyridinyl)methacrylamide to produce 1,2,3,4-tetrahydro-3-methyl-2-oxo-1,6-naphthyridine and then dehydrogenating said tetrahydro compound by heating it in acetic acid. 3-Cyano-2-hydroxy-1,6-naphthyridine, the tautomeric form of 3-cyano-1,6-naphthyridin-2(1H)-one, was reportedly prepared by Hawes et al [J. Med. Chem. 16, 849 (1973)] by refluxing 4-aminonicotinaldehyde and ethyl cyanoacetate in ethanol in the presence of piperidine. The compound was reportedly used as an intermediate for preparing 2-amino-3-cyano-1,6-naphthyridine, a "potential diuretic agent", and is shown as having low diuretic activity.

In another paper Hawes et al [J. Heterocycl. Chem. 11, 151 (1974)] show the preparations of: (a) 3-cyano-1,6-naphthyridin-2(1H)-one by reacting 4-aminonicotinaldehyde with N,N-dimethylcyanoacetamide or 4-cyanoacetylmorpholine in the presence of piperidine; (b) 3-carbamyl-1,6-naphthyridin-2(1H)-one by using malonamide in place of N,N-dimethylcyanoacetamide as in (a); and, (c) 3-carboethoxy-1,6-naphthyridin-2(1H)-one by using diethyl malonate instead of malonamide as in (b).

Moller et al [Ann. 612, 153 (1957)] show as intermediates the 3-R-4-OH-1,6-naphthyridines where R is H, $NH_2$ and COOH.

SUMMARY OF THE INVENTION

In a composition of matter aspect, the invention resides in 5-(lower-alkyl)-3-Q-1,6-naphthyridin-2(1H)-ones or salts thereof, which are useful as cardiotonic agents and/or intermediates, where Q is hydrogen, hydroxy, amino, cyano, carbamyl, carboxy or aminocarbamyl.

In a composition aspect, the invention resides in a cardiotonic composition for increasing cardiac contractility which comprises a pharmaceutically acceptable carrier and, as the active component thereof, a cardiotonically effective amount of 5-(lower-alkyl)-3-Q-1,6-naphthyridin-2(1H)-one or salt thereof, where Q is hydrogen, hydroxy, amino, cyano or carbamyl.

In a method aspect, the invention resides in a method for increasing cardiac contractility in a patient requiring such treatment which comprises administering to such patient a cardiotonically effective amount of 5-(lower-alkyl)-3-Q-1,6-naphthyridin-2(1H)-one or salt thereof, where Q is hydrogen, hydroxy, amino, cyano or carbamyl.

In another composition of matter aspect, the invention resides in 5-(lower-alkanoyl)-3-Q'-6-[2-(di-loweralkylamino)ethenyl]-2(1H)-pyridinones or salt thereof, where Q' is cyano or hydrogen. These compounds where Q is hydrogen are useful as cardiotonic agents and as intermediates, and those where Q' is cyano are useful as intermediates.

In another composition aspect, the invention resides in a cardiotonic composition for increasing cardiac contractility which comprises a pharmaceutically acceptable carrier and, as the active component thereof, a cardiotonically effective amount of 5-(lower-alkanoyl)-6-[2-(di-lower-alkylamino)ethenyl]-2(1H)-pyridinone or salt thereof.

In another method aspect, the invention resides in a method for increasing cardiac contractility in a patient requiring such treatment which comprises administering to such patient a cardiotonically effective amount of 5-(lower-alkanoyl)-6-[2-(di-lower-alkylamino)ethenyl]-2(1H)-pyridinone or salt thereof.

The invention in its process aspects comprises: (a) reacting a 5-(lower-alkanoyl)-3-Q'-6-methyl-2(1H)-pyridinone with di-(lower-alkyl)formamide di-(lower-alkyl) acetal to produce 5-(lower-alkanoyl)-3-Q'-6-[2-(di-lower-alkylamino)ethenyl]-2(1H)-pyridinone (II), where Q' is cyano or hydrogen; (b) reacting II with formamidine or ammonia or salt thereof to produce 3-Q'-5-(lower-alkyl)-1,6-naphthyridin-2(1H)-one, where Q' is cyano or hydrogen; (c) converting 3-cyano-5-(lower-alkyl)-1,6-naphthyridin-2(1H)-one successively to the corresponding 3-carboxy and 3-unsubstituted compounds; (d) converting 3-cyano-5-(lower-alkyl)-1,6-naphthyridin-2(1H)-one to the corresponding 3-carbamyl and 3-aminocarbamyl compounds; (e) converting 3-carbamyl(or aminocarbamyl)-5-(lower-alkyl)-1,6-naphthyridin-2(1H)-one to the corresponding 3-amino-5-(lower-alkyl)-1,6-naphthyridin-2(1H)-one; and, (f) converting said 3-amino compound to the corresponding 3-hydroxy compound.

Another aspect of the invention resides in 1,2-dihydro-5,6-dimethyl-2-oxo-1,6-naphthyridinium 4-methylbenzenesulfonate, useful as a cardiotonic agent.

DETAILED DESCRIPTION INCLUSIVE OF PREFERRED EMBODIMENTS

In a composition of matter aspect the invention resides in 1-R''-3-Q-4-R'-5-R-1,6-naphthyridin-2(1H)-one having the formula I

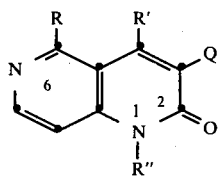

or acid-addition or cationic salt thereof, where R is lower-alkyl, R' is hydrogen or methyl, R'' is hydrogen or lower-alkyl, and Q is hydrogen, hydroxy, amino, cyano, carbamyl, carboxy or aminocarbamyl. The compounds of formula I where Q is hydrogen, hydroxy, amino, cyano or carbamyl are useful as cardiotonic agents, as determined by standard pharmacological evaluation procedures. Preferred embodiments are those of formula I where R is methyl or ethyl, R' and R'' are each hydrogen, and Q is hydrogen, hydroxy, amino or cyano. Particularly preferred embodiments are those of formula I where R is methyl or ethyl, R' and R'' are each hydrogen, and Q is hydrogen. The compounds of formula I where Q is carboxy or aminocarbamyl as well as the compounds where Q is hydrogen, amino, cyano or carbamyl are useful as intermediates as shown hereinbelow.

In another composition of matter aspect, the invention resides in 3-Q'-4-R'-5-(RCO)-6-[2-(di-lower-alkylamino)ethenyl]-2(1H)-pyridinone having the formula II

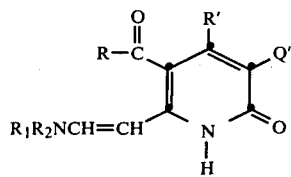

or acid-addition salt thereof, where Q' is hydrogen or cyano, R' is hydrogen or methyl, and R, $R_1$ and $R_2$ are each lower-alkyl. The compounds of formula II where Q' is hydrogen are useful as cardiotonic agents, as determined by standard pharmacological evaluation procedures. The compounds of formula II where Q' is cyano as well as those where Q' is hydrogen are useful as intermediates for preparing said above compounds having formula I where Q is cyano or hydrogen respectively. Preferred embodiments are the compounds of formula II where Q' and R' are each hydrogen, and R, $R_1$ and $R_2$ are each methyl or ethyl.

A composition aspect of the invention resides in the cardiotonic composition for increasing cardiac contractility which comprises a pharmaceutically acceptable carrier and, as the active component thereof, a cardiotonically effective amount of 1-R''-3-Q-4-R'-5-R-1,6-naphthyridin-2(1H)-one having the formula I or pharmaceutically acceptable acid-addition or cationic salt thereof, where R, R' and R'' have the meanings given for formula I and Q is hydrogen, hydroxy, amino, cyano or carbamyl. Preferred embodiments of this aspect of the invention are the compositions having as the active component said compound where R is methyl or ethyl, R' and R'' are each hydrogen, and Q is hydrogen, hydroxy, amino or cyano. Particularly preferred embodiments are those compositions having as active component the compound of formula I where R is methyl or ethyl, R' and R'' are each hydrogen, and Q is hydrogen.

A method aspect of the invention resides in the method for increasing cardiac contractility in a patient requiring such treatment which comprises administering orally or parenterally in a solid or liquid dosage form to such patient a cardiotonically effective amount of 1-R''-3-Q-4-R'-5-R-1,6-naphthyridin-2(1H)-one having the formula I or pharmaceutically acceptable acid-addition or cationic salt thereof, where R, R' and R'' have the meanings given for formula I and Q is hydrogen, hydroxy, amino, cyano or carbamyl. Preferred embodiments are the methods using said compound of formula I where R is methyl or ethyl, R' and R'' are each hydrogen, and Q is hydrogen, hydroxy, amino or cyano. Particularly preferred embodiments are those methods using as active component the compound of formula I where R is methyl or ethyl, R' and R'' are each hydrogen, and Q is hydrogen.

Another composition aspect of the invention resides in the cardiotonic composition for increasing cardiac contractility which comprises a pharmaceutically acceptable carrier and, as the active component thereof, a cardiotonically effective amount of 3-Q'-4-R'-5-(RCO)-6-[2-$R_1R_2$N-ethenyl]-2(1H)-pyridinone of formula II or pharmaceutically acceptable acid-addition salt thereof, where R', R, $R_1$ and $R_2$ have the meanings given for formula II and Q' is hydrogen. Preferred embodiments of this aspect of the invention are the compositions having as the active component said compound of formula II where Q' and R' are each hydrogen, and R, $R_1$ and $R_2$ are each methyl or ethyl.

Another method aspect of the invention resides in the method for increasing cardiac contractility in a patient requiring such treatment which comprises administering orally or parenterally in a solid or liquid dosage form to such patient a cardiotonically effective amount of 3-Q'-4-R'-5-(RCO)-6-[2-($R_1R_2$N)ethenyl]-2(1H)-pyridinone of formula II or pharmaceutically acceptable acid-addition salt thereof, where R', R, $R_1$ and $R_2$ have the meanings given for formula II and Q' is hydrogen. Preferred embodiments of this aspect of the invention are those methods using as active component the compound of formula II where Q' and R' are each hydrogen, and R, $R_1$ and $R_2$ are each methyl or ethyl.

A process aspect of the invention resides in the process which comprises reacting 3-Q'-4-R'-5-(RCO)-6-methyl-2(1H)-pyridinone with di-(lower-alkyl)formamide di-(lower-alkyl) acetal to produce 3-Q'-4-R'-5-(RCO)-6-[2-(di-lower-alkylamino)ethenyl]-2(1H)- pyridinone having formula II above, where Q', R' and R have the meanings given for formula II.

Another process aspect of the invention resides in the process which comprises reacting 3-Q'-4-R'-5-(RCO)-6-[2-(di-lower-alkylamino)ethenyl]-2(1H)-pyridinone of formula II with formamidine or ammonia or salt thereof to produce 3-Q-4-R'-5-R-1,6-naphthyridin-2(1H)-one having formula I where Q and Q', are each cyano or hydrogen, R' is hydrogen or methyl, R is lower-alkyl and R" is hydrogen. The reaction is run preferably using ammonium acetate.

Another process aspect of the invention resides in the process which comprises successively converting 3-cyano-4-R'-5-R-1,6-naphthyridin-2(1H)-one, where R' is hydrogen or methyl and R is lower-alkyl, to the corresponding 3-carboxy and 3-unsubstituted compounds by respectively hydrolyzing the 3-cyano compound to produce the 3-carboxy compound and decarboxylating the 3-carboxy compound.

Another process aspect of the invention resides in the process which comprises successively converting 3-cyano-4-R'-5-R-1,6-naphthyridin-2(1H)-one, where R' is hydrogen or methyl and R is lower-alkyl, to the corresponding 3-carbamyl and 3-aminocarbamyl compounds by respectively hydrolyzing the 3-cyano compound to produce the 3-carbamyl compound and reacting the 3-carbamyl compound with hydrazine to produce the 3-aminocarbamyl compound.

Another process aspect of the invention resides in the process which comprises converting 3-carbamyl or 3-aminocarbamyl-4-R'-5-R-1,6-naphthyridin-2(1H)-one to the corresponding 3-amino-4-R'-5-R-1,6-naphthyridin-2(1H)-one, where R' is hydrogen or methyl and R is loweralkyl, respectively, by reacting the 3-carbamyl compound with a reagent capable of converting carbamyl to amino or by reacting the 3-aminocarbamyl compound with a reagent capable of converting carboxylic acid hydrazide to amino.

Another process aspect of the invention resides in the process which comprises converting 3-amino-4-R'-5-R-1,6-naphthyridin-2(1H)-one to the corresponding 3-hydroxy-4-R'-5-R-1,6-naphthyridin-2(1H)-one, where R' is hydrogen or methyl and R is lower-alkyl, by heating the 3-amino compound with aqueous alkali solution.

Another aspect of the invention resides in 1,2-dihydro-5,6-dimethyl-2-oxo-1,6-naphthyridinium 4-methylbenzenesulfonate, which is useful as a cardiotonic agent.

The term "lower-alkyl" as used herein, e.g., as the meaning of R in formula I or II or of $R_1$ or $R_2$ in formula II or as one of the meanings of R" in formula I means alkyl radicals having from 1 to 4 carbon atoms which can be arranged as straight or branched chains, illustrated by methyl, ethyl, n-propyl, isopropyl, n-butyl, sec.-butyl, tert.-butyl and isobutyl.

The compound of formula I or II is useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. Appropriate pharmaceutically acceptable salts within the scope of the invention are those derived from mineral acids such as hydrochloric acid, hydrobromic acid, sulfuric acid, phosphoric acid and sulfamic acid; and organic acid such as lactic acid, acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said basic compound of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution. The acid-addition salts of said basic compound of formula II are similarly prepared but under anhydrous conditions.

Although pharmaceutically acceptable salts of said basic compound of formula I or II are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

Other pharmaceutically acceptable salts of said compound of formula I are those cationic salts derived from strong inorganic or organic bases, e.g., sodium hydroxide, potassium hydroxide, trimethylammonium hydroxide, to produce the corresponding cationic salt, e.g., sodium, potassium, trimethylammonium salt, respectively.

The molecular structures of the compounds of formulas I and II were assigned on the basis of evidence provided by infrared, ultraviolet, nuclear magnetic resonance and mass spectra, by the correspondence of calculated and found values for the elemental analyses, and, by their method of preparation.

The manner of making and using the instant invention will now be generally described so as to enable a person skilled in the art of pharmaceutical chemistry to make and use the same, as follows.

The reaction of 3-Q'-4-R'-5-(RCO)-6-methyl-2(1H)-pyridinone with di-(lower-alkyl)formamide di-(lower-alkyl) acetal to produce 3-Q'-4-R'-5-(RCO)-6-[2-(di-lower-alkylamino)ethenyl]-2(1H)-pyridinone (II) is carried out by mixing the reactants at about 35° to 100° C.

The preparation of the intermediate 3-Q'-4-R'-5-(RCO)-6-methyl-2(1H)-pyridinones, which are disclosed and claimed in said copending Application Ser. No. 357,872, filed Mar. 15, 1982, are described in the following five paragraphs.

The preparation of 3-Q'-5-(RCO)-6-methyl-2(1H)-pyridinone or 3-Q'-5-(RCO)-4,6-dimethyl-2(1H)-pyridinone, where Q' is hydrogen and R is lower-alkyl is carried out by heating at about 100° C. to 150° C. 2-(RCO)-1-methylethenamine with a lower-alkyl, perferably methyl or ethyl, 2-propynoate or 2-butynoate, respectively, with or without a suitable solvent.

The intermediate 2-(RCO)-1-methyl-ethenamines are generally known compounds which are prepared by conventional means, as illustrated hereinbelow in the specific exemplary disclosure.

The 4-R'-5-(RCO)-6-methyl-1,2-dihydro-2-oxonicotinonitriles or 4-R'-5-(RCO)-6-methyl-1,2-dihydro-2-oxonicotinamides are prepared by a generally known method [Sunthankar et al., Indian J. of Chemistry 11, 1315-16 (1973))] or an improved modification thereof, as illustrated hereinbelow in the specific exemplary disclosure.

The 4-R'-5-(RCO)-6-methyl-1,2-dihydro-2-oxonicotinonitriles or corresponding 4-R'-5-(RCO)-6-methyl-1,2-dihydro-2-oxonicotinamides are conveniently hydrolyzed to produce the correspondingly substituted nicotinic acids under aqueous acidic conditions by heating with aqueous mineral acid, preferably sulfuric acid and preferably at about 70° C. to 130° C. Alternatively, this hydrolysis can be carried out under aqueous alkaline conditions, preferably using aqueous sodium or potassium hydroxide at about 95°–100° C.

Decarboxylation of the 4-R'-5-(RCO)-6-methyl-1,2-dihydro-2-oxonicotinic acids to produce the corresponding 4-R'-5-(RCO)-6-methyl-2(1H)-pyridinones is carried out by heating in the absence or presence of a suitable inert solvent at about 240° C. to 280° C., preferably at about 245° C. to 250° C.

The reaction of II with a formamidine or ammonium salt, preferably acetate, to produce I where Q is hydrogen or cyano, R' is hydrogen or methyl, R" is hydrogen and R is lower-alkyl is carried out by heating the reactants at about 90° C. to 150° C., preferably about 100° C. to 130° C., in a suitable solvent, preferably dimethylformamide, other solvents being acetic acid, n-butanol, para-dioxane, dimethyl sulfoxide, and the like. Preferred salts of formamidine and ammonia are those of weak organic or inorganic acids, for example, acetate, citrate, lactate, tartrate, carbonate, and the like, although salts of strong acids, e.g., hydrochloride and sulfate, also can be used. Optionally and less preferably, the reaction can be run using ammonia under pressure.

The partial hydrolysis of I where Q is cyano to produce I where Q is carbamyl is carried out preferably using concentrated sulfuric acid at about room temperature, i.e., about 20° C. to 30° C. Optionally, other strong inorganic acids, e.g., phosphoric acid, polyphosphoric acid, can be used in place of sulfuric acid.

The hydrolysis of I where Q is cyano to produce I where Q is carboxy is conveniently carried out by heating the cyano compound with aqueous inorganic acid, preferably sulfuric acid, preferably on a steam bath. Optionally, aqueous phosphoric, hydrochloric, hydrobromic or other acids can be used.

Decarboxylation of I where Q is carboxy to produce I where Q is hydrogen is carried out by heating the carboxy compound at about 250° to 280° C. in a suitable inert solvent, for example, eutectic mixture of diphenyl and diphenyl ether (DOWTHERM® A), mineral oil, and the like. Alternatively, I where Q is cyano can be conveniently converted to I where Q is hydrogen in boiling 85% sulfuric acid.

The conversion of I where Q is carbamyl by reaction with hydrazine to produce I where Q is aminocarbamyl is conveniently carried out by heating the carbamyl compound preferably with hydrazine hydrate and neutralizing the reaction mixture with acid, e.g., acetic acid.

The conversion of I where Q is aminocarbamyl to produce I where Q is amino is carried out by reacting the aminocarbamyl compound with a reagent capable of converting carboxylic acid hydrazide to amino. This reaction is run by first reacting the aminocarbamyl compound with nitrous acid in aqueous medium at a low temperature, preferably below 5° C., to form the corresponding compound I where Q is carboxylic acid azide in situ and then stirring the reaction mixture at about 25° to 30° C. until evolution of nitrogen ceases.

The conversion of I where Q is carbamyl to produce I where Q is amino is carried out by reacting the carbamyl compound with a reagent capable of converting carbamyl to amino. The reaction is conveniently run by heating an aqueous mixture containing I where Q is carbamyl and an alkali metal hypohalite, preferably hypobromite or hypochlorite, and then acidifying the reaction mixture, preferably with an aqueous mineral acid, e.g., hydrochloric acid. The reaction can be run initially in an ice bath and then at room temperature up to about 100° C.

The conversion of I where Q is amino to produce I where Q is hydroxy is carried out by heating the amino compound at about 80° C. to 100° C., preferably about 90° C. to 100° C., preferably with aqueous alkali solution, e.g., 5–30% aqueous sodium or potassium hydroxide, and then acidifying the reaction mixture.

The conversin of 4-R'-5-R-1,6-naphthyridin-2(1H)-one (I, Q is H and R" is H) to 1-CH$_3$-4-R'-5-R-1,6-naphthyridin-2(1H)-one (I, Q is H and R" is CH$_3$) by methylation is conveniently carried out by using dimethylformamide dimethyl acetal at about 80° C. to 120° C., preferably about 90° C. to 110° C. and using an aprotic solvent, e.g., dimethylformamide. Other solvents include p-dioxane. Alkylation to produce corresponding 1-R" compounds where R" has from one to four carbon atoms can be run by comparably heating the corresponding 1-unsubstituted compound with a lower-alkyl ester of a strong inorganic or organic sulfonic acid in a suitable solvent, e.g., dimethylformamide, in the presence of an acid-acceptor, e.g., anhydrous potassium carbonate.

The following examples will further illustrate the invention without, however, limiting it thereto.

A.
5-(RCO)-6-METHYL-1,2-DIHYDRO-2-OXONICOTINONITRILES

A-1. 5-Acetyl-1,2-dihydro-6-methyl-2-oxonicotinonitrile

A solution containing 60 g of dimethylformamide dimethyl acetal and 50 g of 2,4-pentanedione was heated on a steam bath for 2.5 hours and cooled. To the resulting solution containing 3-dimethylaminomethylene-2,4-pentanedione was added 300 ml of methanol, 27 g of sodium methoxide and 47 g of cyanoacetamide. The resulting mixture was heated on a steam bath for 4 hours, the hot solution poured into 700 ml of water, and the aqueous mixture acidified with acetic acid and chilled in an ice bath. The solid that separated was collected, dried, and heated with 400 ml. of methanol. Insoluble material was filtered from the hot methanol mixture and the filtrate cooled. The product that separated was collected and dried at 90° C. to produce 24.6 g of 5-acetyl-1,2-dihydro-6-methyl-2-oxonicotinonitrile, m.p. 227°–230° C. [Sunthankar et al., supra, m.p. 231° C.]

A-2. 1,2-Dihydro-6-methyl-2-oxo-5-(n-propanoyl)-nicotinonitrile and 5-acetyl-6-ethyl-1,2-dihydro-2-oxonicotinonitrile A mixture containing 34 g of 2,4-hexanedione, 50 ml of dimethylformamide and 40 ml of dimetylformamide dimethyl acetal was allowed to stand at room temperature overnight and then concentrated on a rotary evaporator at steam bath temperature to yield, as a liquid, 3-dimethylaminomethylene-2,4-hexanedione. A mixture containing said 3-dimethylaminomethylene-2,4-hexanedione, 300 ml of methanol 25.2 g of cyanoacetamide and 16.2 g of sodium methoxide was refluxed with stirring for 3 hours and then concentrated in vacuo to remove the methanol. The residue was dissolved in 300 ml of warm water and filtered. The filtrate was acidified with acetic acid and the resulting precipitate was collected, washed with water, dried in vacuo at 90°–95° C. and recrystallized from dimethylformamide (75 ml) to yield 7.8 g of 1,2-dihydro-6-methyl-2-oxo-5-(n-propanoyl)nicotinonitrile, m.p. 265°–268° C. with decomposition. The mother liquor was concentrated to dryness and digested with hot methanol and cooled. The separated solid was dried, 20.2 g, and recrystallized from dimethylformamide to yield 9.8 g of finely crystalline material, m.p. 259°–263° C. with decomposition. The NMR spectral data for this compound indicated it to be mostly said 1,2-dihydro-6-methyl-2-oxo-5-(n-propanoyl)nicotinonitrile. The resulting mother liquors were combined and concentrated on a rotary eveporator and the resulting residue was recrystallized from ethanol to yield 20.4 g of solid, m.p. 220°–226° C. The NMR spectral data for this solid indicated it to be a 5:4 mixture of said 1,2-dihydro-6-methyl-2-oxo-5-(n-propanoyl)nicotinonitrile and 5-acetyl-6-ethyl-1,2-dihydro-2-oxonicotinonitrile. Preliminary attempts to separate the two compounds by fractional crystallization were unsuccessful; however, the two compounds should be separable.

A-3. 5-Acetyl-1,2-dihydro-6-methyl-2-oxonicotinonitrile and 5-acetyl-1,2-dihydro-6-methyl-2-oxonicotinamide A mixture containing 200 g of 2,4-pentanedione and 300 ml of dimethylformamide dimethyl acetal was heated under reflux on a steam bath for 5 hours and then allowed to stand at room temperature overnight. The excess solvent was distilled off using a rotary evaporator to a constant weight of 307 g, as an oil, of 3-dimethylaminomethylene-2,4-pentanedione which was cobined with 700 ml of methanol and 168 g of cyanoacetamide followed by 108 g of sodium methoxide with stirring and cooling. The reaction mixture was heated under reflux for 7 hours, cooled and treated with 150 ml of glacial acetic acid. The separated solid was collected and the filtrate evaporated to dryness. The residue was treated with 700 ml of water and the insoluble material was collected, washed with water and dried. The two solids were combined and refluxed with 1 liter of methanol. The insoluble beige solid was collected, washed with hot methanol and dried in vacuo at 90°–95° C. to yield 55.8 g of 5-acetyl-1,2-dihydro-6-methyl-2-oxonicotinamide, m.p. >320° C. Both filtrates were concentrated to a volume of about 800 ml and cooled. The separated solid was collected and dried in vacuo at 90°–95° C. to yield 100 g of 5-acetyl-1,2-dihydro-6-methyl-2-oxonicotinonitrile, m.p. 226°–229° C. Further concentration of the mother liquors yielded another 44.2 g of 5-acetyl-1,2-dihydro-6-methyl-2-oxonicotinonitrile, m.p. 221°–225° C.

A-4. 5-Acetyl-1,2-dihydro-4,6-dimethyl-2-oxonicotinonitrile

It is contemplated that this compound can be obtained following the procedure described in Example A-1 using in place of dimethylformamide dimethyl acetal a molar equivalent quantity of dimethylacetamide dimethyl acetal.

B. 5-(RCO)-6-METHYL-1,2-DIHYDRO-2-OXONICOTINIC ACID

B-1. 5-Acetyl-1,2-dihydro-6-methyl-2-oxonicotinic Acid

A mixture containing 34 g of 5-acetyl-1,2-dihydro-6-methyl-2-oxonicotinamide, 50 ml of concentrated sulfuric acid and 100 ml of water was heated on a steam bath with stirring for 6 hours. The hot reaction solution was filtered and to the filtrate was added 50 ml of water. The resulting mixture was allowed to stand at room temperature overnight whereupon the product crystallized out. The separated product was collected, washed with water, dried in a vacuum oven at 90°–95° C. to yield 16.8 g of 5-acetyl-1,2-dihydro-6-methyl-2-oxonicotinic acid, m.p. 238°–241° C. This acid was recrystallized from methanol and dried to yield 14.7 g of 5-acetyl-1,2-dihydro-6-methyl-2-oxonicotinic acid, m.p. 241°–243° C.

B-2. 5-Acetyl-1,2-dihydro-6-methyl-2-oxonicotinic Acid

A mixture containing 52.8 g of 5-acetyl-1,2-dihydro-6-methyl-2-oxonicotinonitrile, 150 ml of water and 75 ml of concentrated sulfuric acid was heated on a steam bath for 15 hours whereupon no reaction took place. The reaction mixture was then heated in a oil bath at 130°–140° C. for six hours allowing the water to evaporate using an air-cooled condenser. The reaction mixture was allowed to stand at room temperature overnight whereupon a white crystalline solid separated. The solid was collected, washed with water and dried in a vacuum oven at 90°–95° C. to yield 49 g of 5-acetyl-1,2-dihydro-6-methyl-2-oxonicotinic acid, m.p. 239°–241° C. To the filtrate was added aqueous ammonia until the pH was about 4 and the solid that separated was collected, washed with water and dried in vacuo at 90°–95° C. to yield another 5.8 g of 5-acetyl-1,2-dihydro-6-methyl-2-oxonicotinic acid, m.p. 238°–241° C.

B-3. 5-Acetyl-1,2-dihydro-4,6-dimethyl-2-oxonicotinic Acid

It is contemplated that this compound can be obtained following the procedure described in Example B-2 but using in place of 5-acetyl-1,2-dihydro-6-methyl-2-oxonicotinonitrile a molar equivalent quantity of 5-acetyl-1,2-dihydro-4,6-dimethyl-2-oxonicotinonitrile.

C. 5-(RCO)-6-METHYL-2(1H)-PYRIDINONES

C-1. 5-Acetyl-6-methyl-2(1H)-pyridinone

A 10 g portion of 5-acetyl-1,2-dihydro-6-methyl-2-oxonicotinic acid was heated neat in a bath of a boiling mixture of diphenyl and diphenyl ether for 40 minutes and the mixture allowed to cool to room temperature. The reaction mixture was dissolved in hot isopropyl alcohol, treated with decolorizing charcoal and filtered, and the filtrate allowed to stand at room temperature for several hours. The separated product was collected and dried at 90°–95° C. to yield 4.3 g of 5-acetyl-6-methyl-2-(1H)-pyridinone, m.p. 193°–195° C.

C-2. 5-Acetyl-4,6-dimethyl-2(1H)-pyridinone

It is contemplated that this compound can be obtained following the procedure described in Example C-1 using in place of 5-acetyl-1,2-dihydro-6-methyl-2- oxonicotinic acid a molar equivalent quantity of 5-acetyl-1,2-dihydro-4,6-dimethyl-2-oxonicotinic acid.

C-3. 5-Acetyl-6-methyl-2(1H)-pyridinone

A mixture containing 100 g of 2,4-pentanedione, 200 ml of ethanol and 60 ml of a concentrated aqueous ammonium hydroxide was allowed to stand at room temperature over the weekend (3 days) and then concentrated on a rotary evaporator to yield 83 g of 4-amino-3-penten-2-one as an oil. To the stirred oil was added 70 ml of methyl 2-propynoate over a 10 minute period and the resulting solution was stirred at ambient temperature for 30 minutes whereupon a vigorous exothermic reaction took place. After the exothermic reaction had subsided, the reaction mixture was heated on a steam bath for 2.5 hours, the reaction mixture was then dissolved in 300 ml of boiling isopropyl alcohol, the solution treated with decolorizing charcoal and filtered, and the filtrate concentrated on a rotary evaporator to yield a viscous liquid. To the viscous liquid was added 300 ml of ether and the mixture triturated and allowed to stand at room temperature overnight. The separated solid was collected, washed with ether and dried to yield 84.6 g of material whose nmr spectrum indicated it to be the uncyclized intermediate, methyl 4-acetyl-5-amino-2,4-hexadienoate. [In another run this compound was isolated, recrystallized from methanol and found to melt at 104°-106° C.] The mother liquor from the above was concentrated on a rotary evaporator to a constant weight of 45.6 g of dark oil. The oil was combined with the uncyclized material and dissolved in 250 ml of dimethylformamide and the resulting mixture was refluxed for 4.5 hours. The reaction mixture was allowed to stand at room temperature overnight whereupon the crystalline product separated. The crystalline precipitate was collected, washed with isopropyl alcohol, dried in a vacuum oven at 90°-95° C. to yield 62.5 g of 5-acetyl-6-methyl-2(1H)-pyridinone, m.p. 196°-198° C. The mother liquor from the above was concentrated to dryness on a rotary evaporator and the residue dissolved in 100 ml of isopropyl alcohol, the alcohol solution treated with decolorizing charcoal and filtered and the filtrate allowed to stand at room temperature overnight. The precipitate that separated was collected to yield another 15.2 g of 5-acetyl-6-methyl-2(1H)-pyridinone, m.p. 194°-196° C.

C-4. 6-Methyl-5-(n-propanoyl)-2(1H)-pyridinone

A mixture containing 25 g of 2,4-hexanedione, 100 ml of ethanol and 25 ml of concentrated aqueous ammonium hydroxide was allowed to stand room temperature overnight and then concentrated on a rotary evaporator to give 21 g, as a pale yellow oil, a mixture containing 4-amino-3-hexen-2-one and 5-amino-4-hexen-3-one. To the oil was added 18.5 g of methyl 2-propynoate and the mixture heated in a oil bath at about 100° whereupon a vigorous exothermic reaction took place. After the reaction had subsided, the reaction mixture was heated in an oil bath at 160°-170° C. for 2 hours and then concentrated on a rotary evaporator to give a gummy material. The latter was crystallized from isopropyl alcohol-ether to yield 64 g of 6-methyl-5-(n-propanoyl)-2(1H)-pyridinone, m.p. 173°-175° C., whose structure was confirmed by its MMR spectrum. No other product was isolated from the mother liquor of the above reaction mixture; however, in another run, Example D-4 hereinbelow, a second product, namely 6-ethyl-5-acetyl-2(1H)-pyridinone was isolated.

C-5. 5-Acetyl-4,6-dimethyl-2(1H)-pyridinone

A mixture containing 40 g of 2,4-pentanedione, 100 ml of ethanol and 50 ml of concentrated aqueous ammonium hyroxide was allowed to stand at room temperature for 6 hours and then concentrated on a rotary evaporator to yield, as an oil, 35.4 g of 4-amino-3-penten-2-one. The oil was dissolved in 100 ml of dimethylformamide and to the solution was added 32 g of methyl 2-butynoate and the resulting reaction mixture was refluxed for 95 hours and then concentrated on a rotary evaporator. The remaining oil residue was heated with 100 ml of ether whereupon a white solid crystallized spontaneously. The solid was collected, washed with ether and dried in a vacuum oven at 90°-95° C. to yield 25.7 g of 5-acetyl-4,6-dimethyl-2(1H)-pyridinone, m.p. 160°-162° C.

C-6. 6-Methyl-5-(n-propanoyl)-2(1H)-pyridinone (and 5-Acetyl-6-ethyl-2(1H)-pyridinone)

A mixture containing 50 g of 2,4-hexanedione, 100 ml of ethanol and 50 ml of concentrated aqueous ammonium hydroxide was allowed to stand at room temperature overnight and then concentrated on a rotary evaporator at 50°-60° C. to a constant weight of 48.8 g, a pale yellow oil that solidified on standing at room temperature. The nmr spectrum of this solid in $CDCl_3$ indicated it to be a mixture of 5-amino-4-hexen-3-one and 4-amino-3-hexen-2-one in a weight ratio of 65:35. The mixture of amino-hexen-ones was dissolved in 100 ml of dimethylformamide and treated with methyl 2-propynoate and the resulting mixture was first gently heated with stirring on a steam bath for 2 hours and then refluxed for 24 hours. The reaction mixture was allowed to cool to room temperature and allowed to stand at room temperature overnight. The crystalline material that separated was collected, washed with isopropyl alcohol and dried in vacuo at 90°-95° C. to yield 11.9 g of 6-methyl-5-(n-propanoyl)-2(1H)-pyridinone, m.p. 173°-175° C. The mother liquor was concentrated on a rotary evaporator and the residue was crystallized from isopropyl alcohol, washed with ether and dried to yield another 10.4 g of 6-methyl-5-(n-propanoyl)-2(1H)-pyridinone, m.p. 173°-175° C. (The filtrate was concentrated in vacuo to yield 57.8 g of an oily residue which was chromatographed on silica gel (700 g) using ether as eluant. Evaporation of the ether fractions yielded 22.4 g of the least polar component, an oily material, a middle fraction of 16.4 g, a viscous gummy oil, and as the most polar component, 7.8 g, a solid which was recrystallized from isopropyl alcohol to yield a white amorphous powder, m.p. 140°-145° C., whose nmr spectrum showed it to consist of 90% 5-acetyl-6-ethyl-2(1H)-pyridinone. Six further recrystallizations of this product resulted in 1.5 g of pure 5-acetyl-6-ethyl-2(1H)-pyridinone, m.p. 162°-164° C., as shown by its nmr spectrum.)

C-7. 5-(n-Butanoyl)-6-methyl-2(1H)-pyridinone

A mixture containing 22.2 g of 3-methyl-5-n-propylisoxazole [Kashima et al., Bull. Chem. Soc. Japan 46, 310-313 (1973)], 500 mg of platinum dioxide and 200 ml of ethanol was hydrogenated under catalytic hydrogenation conditions for ninety minutes, the catalyst was filtered off and the filtrate was concentrated on a rotary evaporator to yield 18.5 g of colorless residue which solidified on cooling. The residue containing 2-amino-2-hepten-4-one was dissolved in 50 ml of dimethylformamide and to the solution was added 14.8 g of methyl 2-propynoate. The resulting reaction solution was allowed to stand at ambient temperature for thirty minutes (exothermic) and then refluxed for three and one half hours. The dimethylformamide was removed on a rotary evaporator. The remaining dark brown liquid was heated in an oil bath at 195°-200° C. for four hours, cooled to room temperature, crystallized from isopropyl alcohol and dried at 80°-85° C. to produce, as pale yellow flakes, 9.4 g of 5-(n-butanoyl)-6-methyl-2(1H)-pyridinone, m.p. 167°-168° C.

Following the procedure described in Example C-7 using in place of 3-methyl-5-n-propylisoxazole a molar equivalent quantity of the appropriate 3-methyl-5-R-isoxazole, it is contemplated that the 5-(RCO)-6-methyl-2(1H)-pyridinones of Examples C-8 and C-9 can be prepared via the appropriate 2-amino-2-alken-4-one.

C-8. 6-Methyl-5-(n-pentanoyl)-2(1H)-pyridinone, first using 5-n-butyl-3-methylisoxazole and then 2-amino-2-octen-4-one C-9. 6-Methyl-5-(3-methylpropanoyl)-2(1H)-pyridinone, first using 5-isopropyl-3-methylisoxazole and then 2-amino-5-methyl-2-hexen-4-one

D.
3-Q'-4-R'-5-(RCO)-6-[2-(DI-LOWER-ALKYLAMINO)ETHENYL]-2(1H)-PYRIDINONES

D-1. 5-Acetyl-6-(2-dimethylaminoethenyl)-2(1H)-pyridinone

A mixture containing 15.1 g of 5-acetyl-6-methyl-2(1H)-pyridinone, 200 ml of dimethylformamide and 15 ml of dimethylformamide dimethyl acetal was stirred at room temperature for 30 minutes, heated gently with stirring on a steam bath for 2 hours, then allowed to cool and stirred at room temperature overnight. The golden yellow needles that separated were collected, washed with methanol and dried in a vacuum oven at 80° C. to yield 10.7 g of 5-acetyl-6-(2-dimethylaminoethenyl)-2(1H)-pyridinone, m.p. 238°-240° C.

Acid-addition salts of 5-acetyl-6-(2-dimethylaminoethenyl)-2(1H)-pyridinone are conveniently prepared by adding to a mixture of 2 g of 5-acetyl-6-(2-dimethylaminoethenyl)-2(1H)-pyridinone in about 40 ml of methanol the appropriate acid, e.g., methanesulfonic acid, concentrated sulphuric acid, concentrated phosphoric acid, to a pH of about 2 to 3, chilling the mixture after a partial evaporation and collecting the precipitated salt, e.g., dimethanesulfonate, sulfate, phosphate, respectively.

D-2. 6-(2-Dimethylaminoethenyl)-5-(n-propanoyl)-2(1H)-pyridinone

A mixture containing 25 g of 6-methyl-5-(n-propanoyl)-2-(1H)-pyridinone, 200 ml of dimethylformamide and 25 ml of dimethylformamide dimethyl acetal was heated on a steam bath for 5 and ½ hours and the dimethylformamide was removed by heating the reaction mixture on a rotary evaporator. The residue was refluxed with 100 ml of ethanol, the mixture cooled, and the yellow solid was collected, washed with ethanol and dried in an oven at 90°-95° C. to yield 12.8 g of 6-(2-dimethylaminoethenyl)-5-(n-propanoyl)-2(1H)-pyridinone, m.p. 204°-206° C.

Acid-addition salts of 6-(2-dimethylaminoethenyl)-5-(n-propanoyl)-2(1H)-pyridinone are prepared following the procedure described in Example D-1.

D-3. 5-Acetyl-1,2-dihydro-6-(2-dimethylaminoethenyl)-2-oxo-3-pyridinecarbonitrile A mixture containing 35.2 g of 5-acetyl-1,2-dihydro-6-methyl-2-oxo-3-pyridinecarbonitrile, 300 ml of methanol and 30 ml of dimethylformamide dimethyl acetal was heated with stirring on a steam bath for 4 and ½ hours and then allowed to cool to room temperature. The precipitated yellow solid was collected, washed with methanol and dried in an oven under reduced pressure at 95° C. to yield 16.4 g of 5-acetyl-1,2-dihydro-6-(2-dimethylaminoethenyl)-2-oxo-3-pyridinecarbonitrile, m.p. 267°-270° C.

Acid-addition salts of 5-acetyl-1,2-dihydro-6-(2-dimethylaminoethenyl)-2-oxo-3-pyridinecarbonitrile can be prepared following the procedure described in Example D-1.

D-4. 1,2-Dihydro-6-(2-dimethylaminoethyl)-2-oxo-5-(n-propanoyl)-3-pyridinecarbonitrile A mixture containing 9.5 g of 1,2-dihydro-6-methyl-2-oxo-5-(n-propanoyl)-3-pyridinecarbonitrile, 50 ml of dimethylformamide and 8 ml of dimethylformamide dimethyl acetal was stirred at room temperature overnight and then concentrated to dryness on a rotary evaporator. The residue was refluxed with isopropyl alcohol; the insoluble yellow solid was collected, washed with isopropyl alcohol and dried at 90° C. to yield 2.8 g of 1,2-dihydro-6-(2-dimethylaminoethenyl)-2-oxo-5-(n-propanoyl)-3-pyridinecarbonitrile, m.p. 278°-280° C. with decomposition. The mother liquor was treated with decolorizing charcoal, filtered and concentrated to about 150 ml and allowed to stand at room temperature. The product that separated was collected, washed with isopropyl alcohol and dried to yield another 1.8 g of product, m.p. 270° C.

Acid-addition salts of 1,2-dihydro-6-(2-dimethylaminoethenyl)-2-oxo-5-(n-propanoyl)-3-pyridinecarbonitrile can be prepared following the procedure described in Example D-1.

D-5. 5-Acetyl-6-(2-diethylaminoethenyl)-2(1H)-pyridinone can be prepared following the procedure described in Example D-2 using in place of dimethylformamide dimethyl acetal a molar equivalent quantity of diethylformamide diethyl acetal.

Following the procedure described in Example D-1 using in place of 5-acetyl-6-methyl-2(1H)-pyridinone a molar equivalent quantity of the appropriate 5-(RCO)-6-methyl-2(1H)-pyridinone, it is contemplated that the compounds of Examples D-6, D-7 and D-8 can be prepared.

D-6. 5-(n-Butanoyl)-6-(2-dimethylaminoethenyl)-2(1H)-pyridinone, using 5-(n-butanoyl)-6-methyl-2(1H)-pyridinone.

D-7. 6-(2-Dimethylaminoethenyl)-5-(n-pentanoyl)-2(1H)-pyridinone,

D-8. 6-(2-Dimethylaminoethenyl)-5-(3-methyl-n-propanoyl)-2(1H)-pyridinone, using 6-methyl-5-(3-methyl-n-propanoyl)-2(1H)-pyridinone.

E.
1-R''-3-Q-4-R'-5-R-1,6-NAPHTHYRIDIN-2(1H)-ONES

E-1. 1,2-Dihydro-5-methyl-2-oxo-1,6-naphthyridine-3-carbonitrile

A mixture containing 33.2 g of 5-acetyl-1,2-dihydro-6-(2-dimethylaminoethenyl)-2-oxo-3-pyridincarbonitrile, 32.1 g of formamidine acetate and 300 ml of dimethylformamide was heated in a oil bath at 120°-130° C. for 3 hours, the original yellow solid dissolving and dark solution resulting. The reaction mixture was evaporated to dryness and then treated with 400 ml of water followed by 30 ml of acetic acid. The resulting insoluble solid was collected, washed with water, air-dried, recrystallized from dimethylformamide and dried at 90° C. to yield 27.4 g of 1,2-dihydro-5-methyl-2-oxo-1,6- naphthyridine-3-carbonitrile as a compound containing ½ mole of dimethylformamide, m.p. 278°–280° C. with decomposition.

The above preparation was also carried out using ammonium acetate in place of formamidine acetate as follows: A mixture containing 1.305 kg of 1,2-dihydro-6-(2-dimethylaminoethenyl)-2-oxo-3-pyridinecarbonitrile, 9 liters of dimethylformamide and 915 g of ammonium acetate was refluxed for five hours. The reaction suspension was cooled to 5° C. for three hours and the precipitated product was collected, washed twice with cold 60/40 by volume of dimethylformamide/water, twice with cold ethanol, once with ether and dried to yield 826 g of 1,2-dihydro-5-methyl-2-oxo-1,6-naphthyridine-3-carbonitrile, m.p. 275°–277° C.

Acid-addition salts and cationic salts of 1,2-dihydro-5-methyl-2-oxo-1,6-naphthyridine-3-carbonitrile can be prepared following the procedure described in Example E-4.

E-2. 1,2-Dihydro-5-methyl-2-oxo-1,6-naphthyridine-3-carboxamide

To 200 ml of concentrated sulfuric acid chilled in an ice bath was added with stirring 37 g of 1,2-dihydro-5-methyl-2-oxo-1,6-naphthyridine-3-carbonitrile and the reaction mixture was allowed to stand at room temperature overnight. The reaction mixture was then poured on ice (1 liter beaker, half filled), the resulting mixture cooled in an ice bath and then neutralized by adding aqueous ammonium hydroxide, followed by addition of acetic acid to make the mixture slightly acidic. The separated solid was collected, washed with water, air-dried, then recrystallized from a large volume of dimethylformamide (1.2 l.) and dried at 95° C. to yield 28.4 g of 1,2-dihydro-5-methyl-2-oxo-1,6-naphthyridine-3-carboxamide, m.p. >320° C.

Acid-addition salts and cationic salts of this 3-carboxamide can be prepared following the procedure described in Example E-4.

E-3. 1,2-Dihydro-5-methyl-2-oxo-1,6-naphthyridine-3-carboxylic acid hydrazide

A mixture containing 34 g of 1,2-dihydro-5-methyl-2-oxo-1,6-naphthyridine-3-carboxamide and 150 ml of hydrazine hydrate was heated on a steam bath for 18 hours and then stripped to dryness on a steam bath. To the residue was added 100 ml of water and the aqueous mixture was neutralized by adding acetic acid. The fine yellow needles were collected, washed successively with water and methanol, and then dried at 90° C. to produce 32.6 g of 1,2-dihydro-5-methyl-2-oxo-1,6-naphthyridine-3-carboxylic acid hydrazide, m.p. >310° C.

E-4. 3-Amino-5-methyl-1,6-naphthyridin-2(1H)-one

To a stirred mixture containing 21.8 g of 1,2-dihydro-5-methyl-2-oxo-1,6-naphthyridine-3-carboxylic acid hydrazide and 100 ml of concentrated sulphuric acid in 200 ml of water was added a solution containing 8 g of sodium nitrite in 30 ml of water over a 30 minute period, maintaining the internal temperature below 5° C. by adding ice to the reaction mixture. The mixture was stirred in an ice bath for about 2 hours and then at room temperature for about 20 hours. The reaction mixture was concentrated to dryness on a rotary evaporator. The residue was treated with 200 ml of water, neutralized by adding small quantities of solid anhydrous potassium carbonate. The resulting yellow solid was collected, washed with water and dried at 90° C. The filtrate was evaporated to dryness and then dissolved in a small quantity of water (about 100 ml) and allowed to stand at room temperature over the weekend. The resulting mixture was evaporated to dryness on a rotary evaporator; the residue was refluxed with 500 ml of dimethylformamide; the mixture was filtered; and, the filtrate was concentrated to dryness to yield a yellow residue which was swirled with 150 ml of water. The solid was collected, washed with water and dried at 90° C. to yield 11.2 g of product. This material was recrystallized from dimethylformamide-ethanol to produce 8.3 g of 3-amino-5-methyl-1,6-naphthyridin-2(1H)-one, m.p. 283°–285° C. with decomposition.

Acid-addition salts of 3-amino-5-methyl-1,6-naphthyridin-2(1H)-one are conveniently prepared by adding to a mixture of 1 g of 3-amino-5-methyl-1,6-naphthyridin-2(1H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after portionally evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 3-amino-5-methyl-1,6-naphthyridin-2(1H)-one and the appropriate acid, e.g., lactic acid or hydrochloric acid, to prepare respectively the lactate or hydrochloride salt of 3-amino-5-methyl-1,6-naphthyridin-2(1H)-one in aqueous solution.

Cationic salts of 3-amino-5-methyl-1,6-naphthyridine-2(1H)-one are conveniently prepared by reaction with an equivalent quantity of the appropriate base, for example, sodium hydroxide, potassium hydroxide or trimethylammonium hydroxide, to produce the corresponding respective sodium, potassium or trimethylammonium salt.

E-5. 3-Hydroxy-5-methyl-1,6-naphthyridin-2-(1H)-one

This compound was prepared by heating 3-amino-5-methyl-1,6-naphthyridin-2(1H)-one following in part the procedure described in Example E-4 without purification of 3-amino-5-methyl-1,6-naphthyridin-2(1H)-one by reacting said unpurified 3-amino compound with aqueous sodium hydroxide solution or by similarly reacting said purified 3-amino compound with aqueous sodium hydroxide solution. These procedures are described as follows. Following the procedure described in Example E-4 using 27 g of 1,2-dihydro-5-methyl-2-oxo-1,6-naphthyridine-3-carboxylic acid hydrazide, 60 ml of concentrated sulfuric acid, 200 ml of water and 9.1 g of sodium nitrite and after concentrating the reaction mixture to dryness on a rotary evaporator, the residue containing the corresponding said 3-amino compound was treated with 75 ml of 35% sodium hydroxide solution and 100 ml of water and the resulting aqueous mixture was heated on a steam bath for 30 hours and then acidified with acetic acid. The acidified mixture was allowed to stand at room temperature overnight and the resulting product that separated was collected, washed with water and air-dried. It was then recrystallized from 400 ml of boiling dimethylformamide, filtering off the insoluble material, concentrating the filtrate to a volume of about 200 ml and then allowing it to stand at room temperature for 3 hours. The yellow crystalline solid was collected, washed with methanol and dried at 100° C. to yield 7.6 g of 3-hydroxy-5-methyl-1,6-naphthyridin-2-(1H)-one, m.p. >320° C. The same compound was also prepared by heating a mixture containing 3-amino-5-methyl-1,6-naphthyridin-2(1H)-one with 25 ml of 10% aqueous sodium hydroxide solution on a steam bath for 7 hours and then cooled to room temperature. The reaction mixture was acidified with acetic acid and the resulting white crystalline precipitate was collected, washed with water and dried at 95° C. to yield 1.2 g of 3-hydroxy-5-methyl-1,6-naphthyridin-2(1H)-one, m.p. >320° C.

Acid-addition salts and cationic salts of 3-hydroxy-5-methyl-1,6-naphthyridine-2(1H)-one can be prepared following the procedure described above in Example E-4.

E-6. 1,2-Dihydro-5-methyl-2-methyl-2-oxo-1,6-naphthyridine-3-carboxylic acid

A mixture containing 63 g of 1,2-dihydro-5-methyl-2-oxo-1,6-naphthyridine-3-carbonitrile, 100 ml of concentrated sulphuric acid and 100 ml of water was heated on a steam bath for 16 hours, after which time tlc analyses (20% methanol in ether) indicated the presence of a considerable amount of starting material. Therefore, the reaction mixture was heated in an oil bath at 135°–140° C. for 8 hours, cooled to room temperature and poured on ice (1 l. beaker, ⅓ filled). The resulting aqueous mixture was neutralized by adding aqueous ammonium hydroxide until slightly basic and was then reacidified by adding acetic acid. The resulting solid was collected, washed successively with water and methanol, and dried at 100° C. to yield 54.8 g of 1,2-dihydro-5-methyl-2-methyl-2-oxo-1,6-naphthyridine-3-carboxylic acid, m.p. 255°–257° C. with decomposition. Another 7.2 g of the product, m.p. 252°–255° C. was obtained from the mother liquor.

E-7a. 5-Methyl-1,6-naphthyridin-2(1H)-one

To 1 l. of boiling eutectic mixture of diphenyl and diphenylether (DOWTHERM ® A) was added over a 5 minute period 55 g of 1,2-dihydro-5-methyl-2-oxo-1,6-naphthyridine-3-carboxylic acid. The reaction mixture was cooled for 5 minutes and then filtered. The filtrate was allowed to stand at room temperature over the weekend. The crystalline material that separated from the filtrate was collected, washed with n-hexane and air-dried to give 38.4 g of material, which was indicated by tlc analysis (20% methanol and ether) to be a mixture. This mixture was chromatographed using 500 g of silica gel in a 1 l. sintered glass funnel using 40% to 60% methanol in ether. The less polar component was recrystallized from isopropyl alcohol to produce 22.4 g of 5-methyl-1,6-naphthyridin-2(1H)-one, m.p. 235°–237° C.

5-Methyl-1,6-naphthyridin-2(1H)-one also was prepared directly from the corresponding 3-cyano compound, as follows: A 650 g portion of 1,2-dihydro-5-methyl-2-oxo-1,6-naphthyridine-3-carbonitrile was added with stirring at room temperature to a solution of 2100 ml 18 M sulfuric acid in 350 ml of water. The reaction mixture was stirred mechanically and refluxed (internal temperature at 215°–220° C.) for 24 hours. The dark solution was allowed to come to ambient temperature and poured on ice. The solution was stirred and basified with 6 l of concentrated ammonium hydroxide to pH 10.5, the internal temperature being maintained at 20°–30° C. during this addition. The dark beige solid was collected by filtration, washed with a minimum of cold water and dried in an oven chamber at 65° overnight. The crude product was recrystallized twice from water with decolorizing charcoal treatment to produce 330 g of 5-methyl-1,6-naphthyridin-2(1H)-one, m.p. 245°–246° C.

Acid-addition salts of 5-methyl-1,6-naphthyridin-2(1H)-one are conveniently prepared by adding to a mixture of 2 g of 5-methyl-1,6-naphthyridin-2(1H)-one in about 40 ml of aqueous methanol the appropriate acid, e.g., methanesulfonic acid, concentrated sulphuric acid, concentrated phosphoric acid, to a pH of about 2 to 3, chilling the mixture after partial evaporation and collecting the precipitate, e.g, dimethanesulfonate, sulphate, phosphate, respectively. Also, the acid-addition salt is conveniently prepared in aqueous solution by adding to water with stirring molar equivalent quantities each of 5-methyl-1,6-naphthyridin-2-(1H)-one and the appropriate acid, e.g., lactic acid or hydrochloric acid, to prepare respectively the monolactate or monohydrochloride salt in aqueous solution.

Cationic salts of 5-methyl-1,6-naphthyridin-2(1H)-one are conveniently prepared by reaction with an equivalent quantity of the appropriate base, for example, sodium hydroxide, potassium, hydroxide or trimethylammonium hydroxide, to produce the corresponding respective sodium, potassium or trimethylammonium salt.

E-7b. 5-Methyl-1,6-naphthyridin-2(1H)-one

A mixture containing 10.3 g of 5-acetyl-6-(2-dimethylaminoethenyl)-2(1H)-pyridinone, 10.4 g of formamidine acetate and 75 ml of dimethylformamide was heated on a steam bath for 5 hours and then concentrated to dryness on a rotary evaporator. The residue was treated with 50 ml of water and again stripped to dryness. The white residue was recrystallized from isopropyl alcohol to yield 6.7 g of 5-methyl-1,6naphthyridin-2(1H)-one, m.p. 238°–240° C. This compound was the same as the compound of Example E-7a, e.g., a mixed melting point showed no depression and the infrared and nuclear magnetic resonance spectral data for the compounds were respectively the same.

E-8. 5-Ethyl-1,6-naphthyridin-2(1H)-one

A mixture containing 8.2 g of 6-(2-dimethylaminoethenyl)-5-(n-propanoyl)-2(1H)-pyridinone, 3.9 of formamidine acetate and 100 ml of dimethylformamide was refluxed in an oil bath for 5 hours and then evaporated to dryness on a rotary evaporator. The residue was recrystallized from ethanol and dried at 90°–95° C. to yield 5.5 g of product, m.p. 182°–184° C. This product was recrystallized from isopropyl alcohol and dried at 90°–95° C. to produce 4.4 g of 5-ethyl-1,6-naphthyridin-2(1H)-one, m.p. 186°–188° C.

Acid-addition salts and cationic salts of this compound can be prepared following the procedure described in Example E-7a.

E-9. 1,5-Dimethyl-1,6-naphthyridin-2(1H)-one

A mixture containing 4.5 g of 5-methyl-1,6-naphthyridin-2(1H)-one, 15 ml of dimethylformamide and 4 ml of dimethylformamide dimethyl acetal was stirred at room temperature overnight, then heated on a steam bath for 7 hours and then evaporated to dryness on a rotary evaporator. The solid residue was recrystallized from isopropyl alcohol and dried at 90°–95° C. to yield 3.5 g of 1,5-dimethyl-1,6-naphthyridin-2(1H)-one, m.p. 203°–205° C.

E-10. 1,2-Dihydro-5,6-dimethyl-2-oxo-1,6-naphthyridinium 4-Methylbenzenesulphonate A mixture containing 8 g of 5-methyl-1,6-naphthyridin-2(1H)-one, 12 g of methyl 4-methylbenzenesulphonate and 100 ml of dimethylformamide was heated on a steam bath for 5 hours and then concentrated on a rotary evaporator. The solid residue was refluxed with 100 ml of methanol, the product collected and dried at 90°–95° C. to produce 13.6 g of 1,2-dihydro-5,6-dimethyl-2-oxo-1,6-naphthyridinium 4-methylbenzensulphonate, m.p. 253°–255° C.

Following the procedure described in Example 7b but using in place of 5-acetyl-6-(2-dimethylaminoethenyl)-2(1H)-pyridinone a molar equivalent quantity of the appropriate 5-(RCO)-6-[2-(R$_1$R$_2$N)ethenyl]-2(1H)-pyridinone and in place of formamidine acetate a molar equivalent quantity of ammonium acetate, it is contemplated that the compounds of Examples E-11 through E-14 can be obtained.

E-11. 5-n-Propyl-1,6-naphthyridin-2-(1H)-one, using 5-(n-butanoyl)-6-(2-dimethylaminoethenyl)-2(1H)-pyridinone.

E-12. 5-Methyl-1,6-naphthyridin-2(1H)-one, using 5-acetyl-6-(2-diethylaminoethenyl)-2(1H)-pyridinone.

E-13. 5-n-Butyl-1,6-naphthyridin-2(1H)-one, using 6-(2-dimethylaminoethenyl)-5-(n-pentanoyl)-2(1H)-pyridinone.

E-14. 5-Isopropyl-1,6-naphthyridin-2(1H)-one, using 6-(2-dimethylaminoethenyl)-5-(3-methyl-n-propanoyl)-2(1H)-pyridinone.

The usefulness of the compounds of formula I where Q is hydrogen, hydroxy, amino, cyano or carbamyl and the compounds of formula II where Q' is hydrogen as cardiotonic agents is demonstrated by their effectiveness in standard pharmacological test procedures, for example, in causing a significant increase in contractile force of the isolated cat or guinea pig atria and papillary muscle and/or in causing a significant increase in cardiac contractile force in the anesthetized dog with lower or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I where Q is hydrogen, hydroxy, amino, cyano or carbamyl and the compounds of formula II where Q' is hydrogen at doses of 0.3, 1, 10, 30 and/or 100 μg/ml., were found to cause significant increases, that is, greater than 25% (cat) or 30% (g.pig) in papillary muscle force and significant increases, that is, greater than 25% (cat) or 30% (g.pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested by said guinea pig atria and papillary muscle procedure, the following illustrative compounds were found to cause respective papillary muscle force and right atrial force increases as follows: Example D-1, 62% and 75% at 30 μg/ml, and 111% and 195% at 100 μg/ml; Example D-2, 43% and 100% at 30 μg/ml, and 86% and 195% at 100 μg/ml; Example E-4, 40% and 47% at 3 μg/ml, 135% and 77% at 10 μg/ml, and 119% and 168% at 30 μg/ml; Example E-5, 85% and 54% at 10 μg/ml, and 68% and 45% at 30 μg/ml; Example E-9, 102% and 199% at 100 μg/ml; Example E-10, 94% and 90% at 100 μg/ml; Example E-7a, 63% and 47% at 1 μg/ml, 87% and 88% at 3 μg/ml; and 102% and 116% at 10 μg/ml; and, Example E-8, 87% and 67% at 0.3 μg/ml, 130% and 107% at 1 μg/ml and 136% and 129% at 3 μg/ml. When tested by said corresponding cat atria and papillary muscle procedure, the following illustrative compounds were found to cause respective papillary muscle force and right atrial force increases as follows: Example E-1, 96% and 53% at 10 μg/ml; and, Example E-2, 83% and 18% at 100 μg/ml.

When tested by said anesthetized dog procedure, the compounds of formula I where Q is hydrogen, hydroxy, amino, cyano or carbamyl and the compounds of formula II where Q' is hydrogen at doses of 0.01, 0.03, 0.10, 0.30, 1.0 and/or 3.0 mg/kg administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples D-1, E-4, E-5, E-7a, E-8 and E-9 were found to cause increases of about 32% to 200% in contractile force and lower changes in heart rate and blood pressure.

The present invention includes within its scope a cardiotonic composition for increasing cardiac contractility, said composition comprising a pharmaceutically acceptable carrier and, as the active component thereof, the compound of formula I where Q is hydrogen, hydroxy, amino, cyano or carbamyl or the compound of formula II where Q' is hydrogen. The invention also includes within its scope the method for increasing cardiac contractility in a patient requiring such treatment which comprises administering to such patient a cardiotonically effective amount of the compound of formula I where Q is hydrogen, hydroxy, amino, cyan or carbamyl or the compound of formula II where Q' is hydrogen. In clinical practice said compound will normally be administered orally or parenterally in a wide variety of dosage forms.

Solid compositions for oral administration include compressed tablets, pills, powders and granules. In such solid composition, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied to that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 3-Q'-4-R'-5-(RCO)-6-[2-(di-lower-alkylamino)ethenyl]-2(1H)-pyridinone having the formula

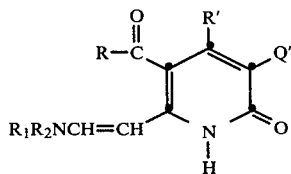

or acid-addition salt thereof, where Q' is hydrogen or cyano, R' is hydrogen or methyl, and R, $R_1$ and $R_2$ are each lower-alkyl.

2. A compound according to claim 1 where Q' and R' are each hydrogen, and R, $R_1$ and $R_2$ are each methyl or ethyl.

3. 5-Acetyl-6-(2-dimethylaminoethenyl)-2(1H)-pyridinone according to claim 1.

4. 6-(2-Dimethylaminoethenyl)-5-(n-propanoyl)-2(1H)-pyridinone according to claim 1.

5. 5-Acetyl-1,2-dihydro-6-(2-dimethylaminoethenyl)-2-oxo-3-pyridinecarbonitrile according to claim 1.

6. 1,2-Dihydro-6-(2-dimethylaminoethenyl)-2-oxo-5-(n-propanoyl)-3-pyridinecarbonitrile according to claim 1.

7. A cardiotonic composition for increasing cardiac contractility which comprises a pharmaceutically acceptable carrier and, as the active component thereof, a cardiotonically effective amount of the 3-Q'-4-R'-5-(RCO)-6-[2-($R_1R_2$N)ethenyl]-2(1H)-pyridinone of claim 1 or pharmaceutically acceptable acid-addition salt thereof, where R', R, $R_1$ and $R_2$ have the meanings given in claim 1 and Q' is hydrogen.

8. A cardiotonic composition according to claim 7 where in the active component Q' and R' are each hydrogen, and R, $R_1$ and $R_2$ are each methyl or ethyl.

9. A cardiotonic composition according to claim 7 where the active component is 5-acetyl-6-(2-dimethylaminoethenyl)-2(1H)-pyridinone.

10. A cardiotonic composition according to claim 7 where the active component is 6-(2-dimethylaminoethenyl)-5-(n-propanoyl)-2(1H)-pyridinone.

11. A method for increasing cardiac contractility in a patient requiring such treatment which comprises administering orally or parenterally in a solid or liquid dosage form to such patient a cardiotonically effective amount of the 3-Q'-4-R'-5-(RCO))-6-[2-($R_1R_2$N)-ethenyl]-2(1H)-pyridinone of claim 1 or pharmaceutically acceptable acid-addition salt thereof, where R', R, $R_1$ and $R_2$ have the meanings given in claim 1 and Q' is hydrogen.

12. A method according to claim 11 where in the active component Q' and R' are each hydrogen, and R, $R_1$ and $R_2$ are each methyl or ethyl.

13. The method according to claim 11 where the active component is 5-acetyl-6-(2-dimethylaminoethenyl)-2(1H)-pyridinone.

14. The method according to claim 11 where the active component is 6-(2-dimethylaminoethenyl)-5-(n-propanoyl)-2(1H)-pyridinone.

* * * * *

UNITED STATES PATENT AND TRADEMARK OFFICE
CERTIFICATE OF CORRECTION

PATENT NO. : 4,415,580

DATED : November 15, 1983

INVENTOR(S) : G. Y. Lesher et al.

It is certified that error appears in the above-identified patent and that said Letters Patent is hereby corrected as shown below:

Abstract, face page, line 9, " Q" " should read -- Q' --.

Column 2, line 10, "carboethoxy" should read -- carbethoxy --.

Column 6, lines 64-65, "perferably" should read -- preferably --.

Signed and Sealed this

Twenty-eighth Day of May 1985

[SEAL]

Attest:

DONALD J. QUIGG

Attesting Officer

Acting Commissioner of Patents and Trademarks